US00PP15743P2

(12) United States Plant Patent
Hanes

(10) Patent No.: US PP15,743 P2
(45) Date of Patent: May 3, 2005

(54) ***VERBENA* PLANT NAMED 'RAP BURG TWO'**

(50) Latin Name: ***Verbena hybrida*×*Verbena tenuisecta***
Varietal Denomination: Rap Burg Two

(75) Inventor: Mitchell Hanes, Morgan Hill, CA (US)

(73) Assignee: Goldsmith Seeds, Inc, Gilroy, CA (US)

( * ) Notice: Subject to any disclaimer, the term of this patent is extended or adjusted under 35 U.S.C. 154(b) by 26 days.

(21) Appl. No.: 10/818,504

(22) Filed: Apr. 5, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Rap Burg Two', characterized by its compact, low and outwardly spreading, and decumbent plant habit; freely branching habit; early and uniform flowering habit and dark red purple-colored flowers.

1 Drawing Sheet

Botanical classification/cultivar designation: *Verbena hybrida*×*Verbena tenuisecta* cultivar Rap Burg Two.

BACKGROUND OF THE INVENTION

The present Invention relates to a new and distinct cultivar of *Verbena* plant, botanically known as *Verbena hybrida*×*Verbena tenuisecta,* and hereinafter referred to by the name 'Rap Burg Two'.

The new *Verbena* is a product of a planned breeding program conducted by the Inventor in Gilroy, Calif. The objective of the breeding program is to develop new compact *Verbena* cultivars with early and uniform flowering, good basal branching, attractive flower and foliage coloration, and tolerance to Powdery Mildew.

The new *Verbena* originated from a cross-pollination made by the Inventor in March, 2001 of the *Verbena hybrida* cultivar Vertis, disclosed in U.S. Plant Pat. No. 12,288, as the female, or seed, parent with a proprietary *Verbena tenuisecta* selection identified as code number 99-1042-3, not patented, as the male, or pollen, parent. The cultivar Rap Burg Two was discovered and selected by the Inventor as a flowering plant within the progeny from this cross-pollination in a controlled environment in Gilroy, Calif. in September, 2001.

Asexual reproduction of the new cultivar by terminal cuttings in Gilroy, Calif., since September, 2001 has shown that the unique features of this new *Verbena* are stable and reproduced true to type in successive generations of asexual reproduction.

SUMMARY OF THE INVENTION

The following traits have been repeatedly observed and are determined to be the unique characteristics of 'Rap Burg Two'. These characteristics in combination distinguish 'Rap Burg Two' as a new and distinct cultivar:

1. Compact, low and outwardly spreading, and decumbent plant habit.
2. Freely branching habit.
3. Early and uniform flowering habit.
4. Dark red purple-colored flowers.
5. Relatively less susceptible to Powdery Mildew.

In side-by-side comparisons conducted in Gilroy, Calif., plants of the new *Verbena* differed from plants of the female parent, the cultivar Vertis, in the following characteristics:

1. Plants of the new *Verbena* were more compact than plants of the cultivar Vertis.
2. Plants of the new *Verbena* and the cultivar Vertis differed in flower coloration as plants of the cultivar Vertis had white-colored flowers.

In side-by-side comparisons conducted in Gilroy, Calif., plants of the new *Verbena* differed from plants of the male parent selection in the following characteristics:

1. Plants of the new *Verbena* had narrower leaves than plants of the male parent selection.
2. Plants of the new *Verbena* and the male parent selection differed in flower color as plants of the male parent selection had purple-colored flowers.

The new *Verbena* can be compared to the cultivar, Esca Burg Two, disclosed in U.S. Plant Pat. No. 13,988. However, in side-by-side comparisons conducted in Gilroy, Calif., plants of the new *Verbena* differed from plants of the cultivar Esca Burg Two in the following characteristics:

1. Plants of the new *Verbena* had shorter internodes than plants of the cultivar Esca Burg Two.
2. Leaves of plants of the new *Verbena* were smaller and more deeply dissected than leaves of plants of the cultivar Esca Burg Two.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Rap Burg Two'.

The photograph at the bottom of the sheet is a close-up view of typical flower racemes and leaves of 'Rap Burg Two'.

Flower and foliage colors in the photographs may differ slightly from the color values cited in the detailed botanical description which accurately describe the colors of the new *Verbena*.

DETAILED BOTANICAL DESCRIPTION

Plants of the cultivar Rap Burg Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures about 24 to 32° C., night temperatures about 13 to 18° C. and light levels about 2,000 foot-candles. Plants used for the photographs and description were about twelve weeks from planting rooted cuttings and were pinched twice. In the following description, color references are made to The Royal Horticultural Society Colour Chart, 1995 Edition, except where general terms of ordinary dictionary significance are used.

Botanical classification: *Verbena hybrida*×*Verbena tenuisecta* cultivar Rap Burg Two.

Parentage:

*Female, or seed, parent.*—*Verbena hybrida* cultivar Vertis, disclosed in U.S. Plant Pat. No. 12,288.

*Male, or pollen, parent.*—Proprietary *Verbena tenuisecta* selection identified as code number 99-1042-3, not patented.

Propagation:

*Type cutting.*—Terminal cuttings.

*Time to initiate roots.*—About 7 to 10 days at 22 to 24° C.

*Time to produce a rooted cutting or liner.*—About three to four weeks at 22 to 24° C.

*Root description.*—Fine, fibrous; white in color.

*Rooting habit.*—Freely branching.

Plant description:

*Form.*—Compact, low and outwardly spreading, and decumbent plant habit.

*Growth and branching habit.*—Moderately vigorous and freely-branching with about six main stems and multiple secondary lateral branches.

*Plant height.*—About 16 cm.

*Plant diameter or spread.*—About 54 cm.

*Lateral branches.*—Length: About 36 cm. Diameter: About 2.5 mm. Internode length: Vegetative branches, about 2 cm; reproductive branches, about 5 cm. Strength: Strong. Texture: Pubescent. Color: 146B.

*Foliage description.*—Arrangement: Opposite, simple. Length: About 4.5 cm. Width: About 5.2 cm. Shape: Deltoid; highly dissected, fern-like. Apex: Acute. Base: Attenuate. Margin: Deeply dissected. Texture, upper and lower surfaces: Coarse, pubescent. Venation pattern: Pinnate, netted. Color: Developing and fully expanded foliage, upper surface: 147A. Developing and fully expanded foliage, lower surface: 147B. Venation, upper and lower surfaces: 147B. Petiole: Length: About 1.5 cm. Diameter: About 2 mm. Color: 146B.

Flower description:

*Flower type and habit.*—Single upright salverform flowers arranged on terminal racemes; flowers sessile. Freely flowering with about 50 flowers per raceme; about three racemes per lateral branch. Inflorescences positioned above and beyond the foliage. Flowers last about five to seven days under greenhouse conditions. Flowers not persistent.

*Fragrance.*—None detected.

*Flowering season.*—In the garden, flowering is continuous from spring until fall.

*Inflorescence size.*—Height: About 4 cm. Diameter: About 4 cm.

*Flower size.*—Diameter: About 1.4 cm. Tube length: About 2 cm.

*Flower buds.*—Length: About 1.2 cm. Diameter: About 2 mm. Shape: Tubular. Color: Darker than 77A.

*Petals.*—Quantity/arrangement: Five per flower fused at base. Lobe length: About 7 mm. Lobe width: About 5 mm. Shape: Cordate. Apex: Emarginate. Margin: Entire. Texture, upper and lower surfaces: Velvety, smooth. Color: When opening, upper surface: Slightly darker than 71A. When opening, lower surface: 77A. Fully opened, upper surface: Darker than 71A; towards the center, close to 150B. Fully opened, lower surface: 77A. Throat: Close to 150B.

*Sepals.*—Quantity/arrangement: Five, fused into a tube. Length: About 1 cm. Diameter: Less than 1 mm. Shape: Ligulate. Apex: Acuminate. Margin: Entire. Texture, upper and lower surfaces: Coarse, pubescent. Color, upper surface: 146A to 148A. Color, lower surface: 148B.

*Peduncles.*—Length: About 6 cm. Diameter: About 1 mm. Angle: Upright or curving upward on horizontal stems. Strength: Strong. Color: 144A.

*Reproductive organs.*—Stamens: Quantity: Four. Anther shape: Ovoid. Anther length: Less than 1 mm. Anther color: 145A. Pollen amount: Scarce. Pollen color: 150A. Pistils: Quantity: One. Pistil length: About 1.5 cm. Stigma shape: Bi-parted. Stigma color: 145B. Style length: About 1.3 cm. Style color: 145D. Ovary color: 145B.

*Fruit/seed.*—Fruit and seed production has not been observed.

Disease/pest resistance: Plants of the new *Verbena* have been observed to be relatively less susceptible to Powdery Mildew. Plants of the new *Verbena* have not been observed to be resistant to other pathogens and pests common to *Verbena*.

Temperature tolerance: Plants of the new *Verbena* have been observed to be tolerant to temperatures ranging from 2 to 40° C.

It is claimed:

1. A new and distinct cultivar of *Verbena* plant named 'Rap Burg Two', as illustrated and described.

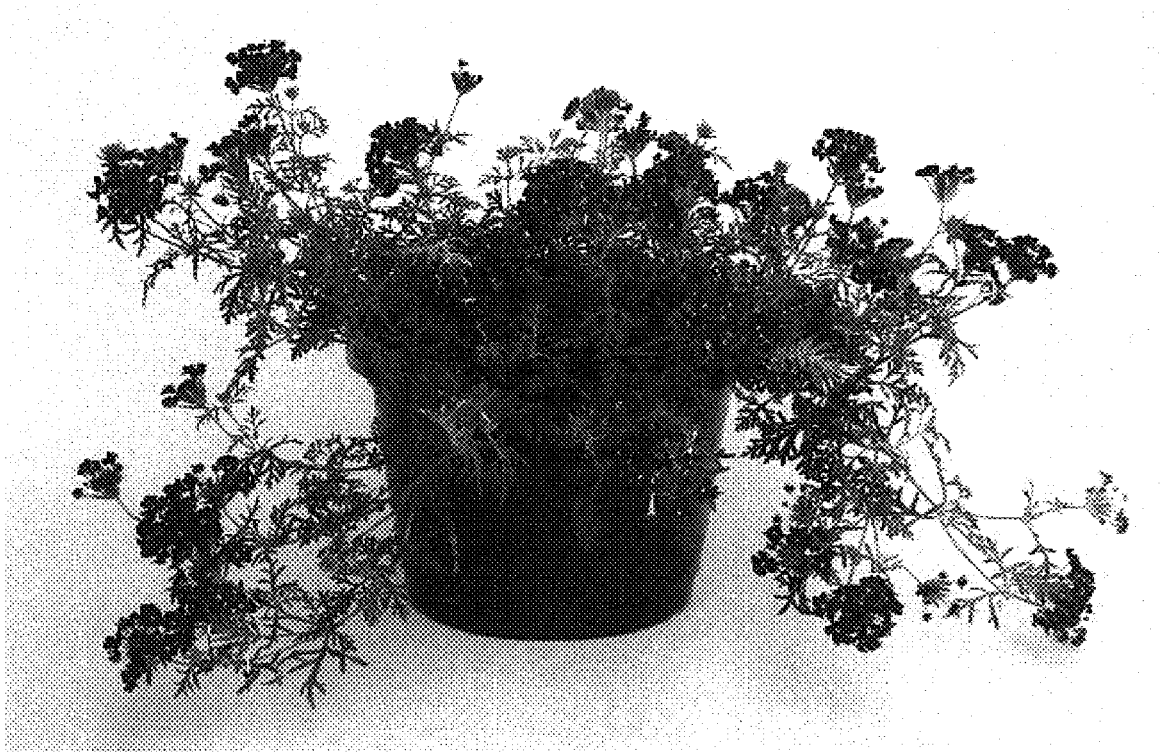
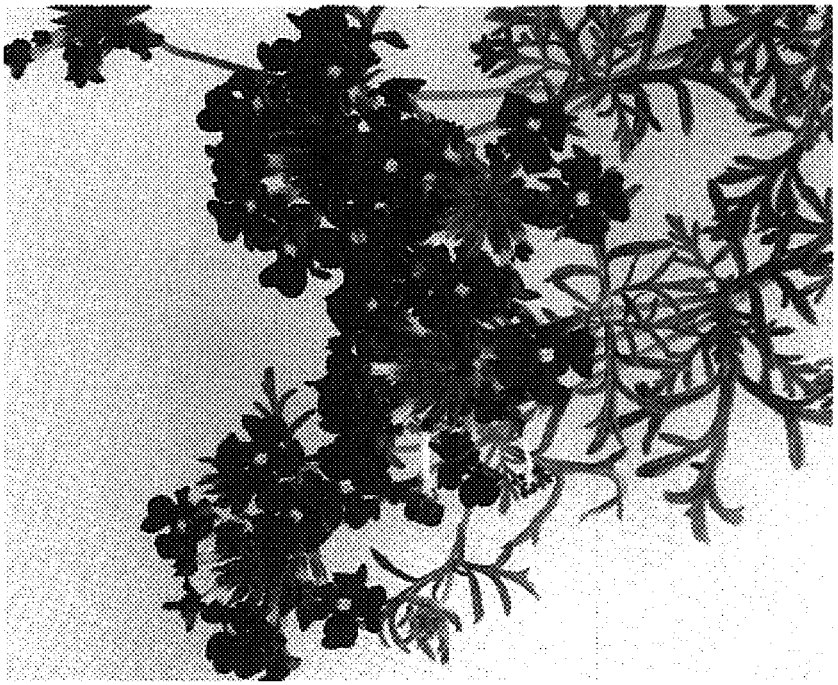

* * * * *